United States Patent [19]
Stabel et al.

[11] Patent Number: 5,969,195
[45] Date of Patent: Oct. 19, 1999

[54] HYDROLYSIS OF ALKYL MONOHALIDES

[75] Inventors: Uwe Stabel, Otterstadt; Gerhard Fahrbach, Plankstadt; Werner Neumann, Ludwigshafen, all of Germany

[73] Assignee: BASF Aktiengesellschaft, Ludwigshafen, Germany

[21] Appl. No.: 09/076,134

[22] Filed: May 12, 1998

[30] Foreign Application Priority Data

May 21, 1997 [DE] Germany ............................ 197 21 301

[51] Int. Cl.[6] .................................................. C07C 27/10
[52] U.S. Cl. ................................ 568/700; 568/16; 568/6
[58] Field of Search .................... 568/700, 16, 6

[56] References Cited

U.S. PATENT DOCUMENTS

| | | | |
|---|---|---|---|
| 1,641,544 | 9/1927 | MacMullin | 568/700 |
| 1,688,726 | 10/1928 | McKee | 568/700 |
| 4,713,413 | 12/1987 | Tegge et al. | 568/700 |
| 5,490,919 | 2/1996 | Pri-Bar et al. | 208/262 |

FOREIGN PATENT DOCUMENTS

| | | |
|---|---|---|
| 479350 | 4/1992 | European Pat. Off. . |
| 694328 | 4/1995 | European Pat. Off. . |
| 726306 | 2/1996 | European Pat. Off. . |

*Primary Examiner*—Louise N. Leary
*Attorney, Agent, or Firm*—Keil & Weinkauf

[57] ABSTRACT

A process for hydrolyzing alkyl monohalides comprises using activated carbon impregnated with alkali metal hydroxide or alkaline earth metal hydroxide in the presence of water and converting the alkyl monohalides virtually quantitatively into the corresponding alcohols. Apparatus for carrying out the process comprises at least one, preferably two, especially three, reactors (2), especially tubular reactors. The process is also particularly useful for preparing alcohols.

10 Claims, 1 Drawing Sheet

F I G U R 1
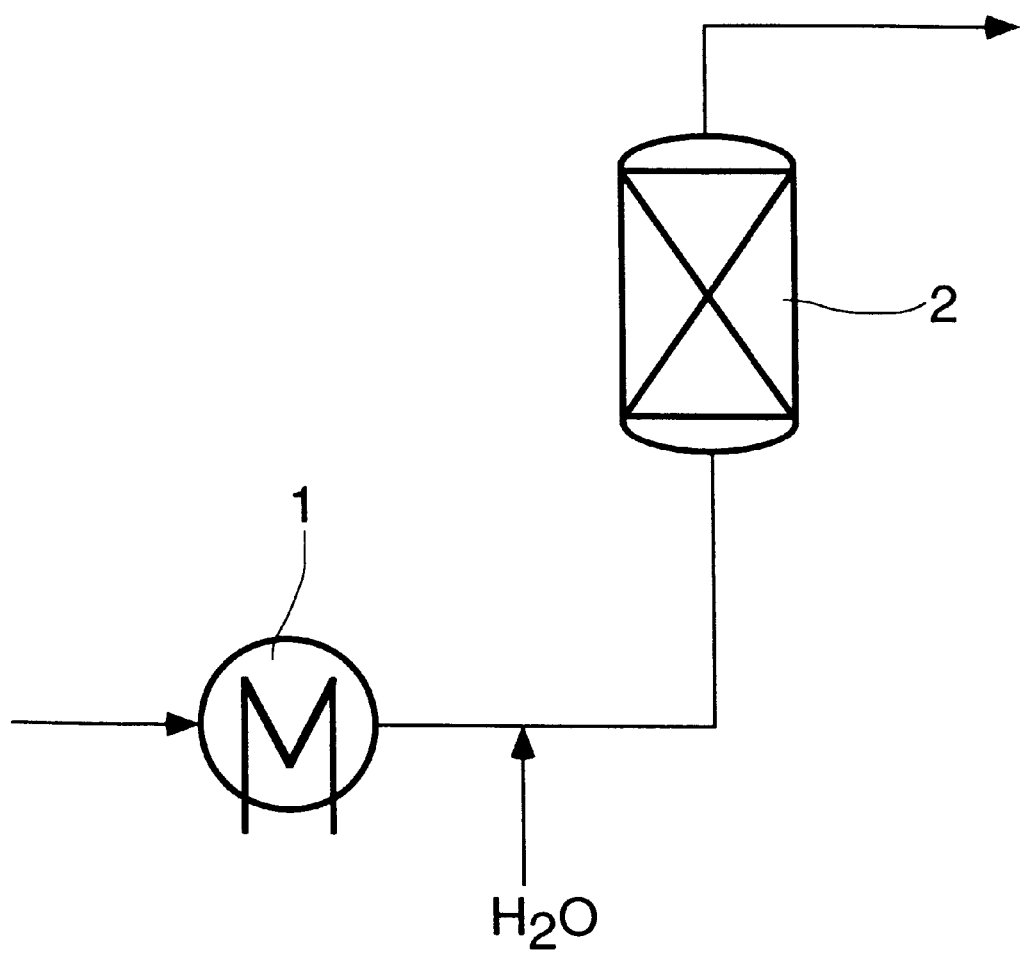

HYDROLYSIS OF ALKYL MONOHALIDES

The present invention relates to the hydrolysis of alkyl monohalides in a mixture comprising said alkyl monohalides, to an apparatus for carrying out the process and to a use.

Alkyl halides are formed in process gases or secondary streams of reactions in which chlorine, chlorides or PVC are used or, for example, in waste gases from plastics recycling plants that process PVC-comprising materials. Owing to their toxic effect, organohalogen compounds cannot just be discharged into the atmosphere, and for the gases or secondary streams to be further used, for example as fuel or as feedstock for further chemical processes such as steam crackers or in refineries, low values of organic chlorine are vital.

A multiplicity of processes are known for converting organohalogen compounds into halogen-free hydrocarbons.

EP-A-726 306 describes a catalytic hydrogenation process involving hydrogen for gases which may comprise chlorinated hydrocarbons over noble metal catalysts, especially cobalt-molybdenum or nickel-molybdenum catalysts.

Disadvantages are the catalyst on-stream time problem, the possibility of the active components being poisoned, for example by sulfur, the need to add hydrogen and the formation of corrosive hydrogen chloride.

U.S. Pat. No. 5,490,919 describes, for example, the dehalogenation of chlorine-, fluorine- or bromine-containing organohalides by reaction with an alkali metal hydroxide, especially sodium hydroxide or potassium hydroxide, in alcoholic solution in the presence of catalytic amounts of a dehydrogenation catalyst, for example palladium/carbon, at temperatures between 50 and 150° C. and atmospheric pressure. Disadvantages are the catalyst on-stream time problem on account of the active component palladium and the need to add extraneous alcohols as solvents.

EP-A-0 694 328 describes a process for purifying halogen-containing waste gases from a trash incinerator by absorption in a migrating bed of calcium oxide and/or calcium hydroxide which may include from 2 to 20% by weight of activated carbon. Better than 99% removal of HCl is achieved. The particular disadvantage is the solids handling. Waste gases from trash incinerators comprise chlorine predominantly in the form of hydrogen chloride, and the effectiveness of the process described has not been demonstrated for higher concentrations of organohalogen compounds.

It is an object of the present invention to provide a hydrolysis process which is simple and safe and ensures high degrees of conversion in respect of monosubstituted alkyl halides even in higher concentrations. The process of the invention shall manage with technically simple processing apparatus, without on-stream time problems (poisoning), and with reagents which are simple to handle and inexpensive. The formation of hydrogen chloride shall be avoided and hence the use of corrosion-resistant specialty materials for the processing apparatus. Alkyl monohalides from, for example, process gases shall be converted in an almost quantitative yield into the corresponding alcohols.

We have found that this object is achieved by conducting the hydrolysis of the mixture comprising alkyl monohalides in the presence of water over activated carbon impregnated with alkali metal hydroxide or alkaline earth metal hydroxide.

The activated carbon impregnated with alkali metal hydroxide or alkaline earth metal hydroxide acts as an hydrolysis activator which effects the almost quantitative conversion of the alkyl monohalides into alcohols.

It is surprising that organic halogen compounds turn out to be readily hydrolyzable over activated carbon impregnated with alkali metal hydroxide or alkaline earth metal hydroxide.

The process of the invention can be applied with particular advantage to the lower primary alkyl halides, especially to $C_1$–$C_4$-alkyl monohalides, preferably to $C_1$–$C_3$-alkyl monohalides, and to mixtures comprising $C_1$–$C_4$-alkyl monohalides, preferably $C_1$–$C_3$-alkyl monohalides.

The process of the invention provides for at least 99% conversion of the thermally particularly stable lower primary organic chlorides, such as methyl chloride, ethyl chloride and n-propyl chloride, into the corresponding alcohol. The process is similarly useful for hydrolyzing the corresponding bromides and iodides, which are simpler to convert, since they are thermally not so stable.

It is particularly advantageous to impregnate the activated carbon with aqueous solutions of from 1 to 40% by weight, especially from 5 to 25% by weight, of alkali metal hydroxide or alkaline earth metal hydroxide. Sodium hydroxide is advantageous to use.

It is a further advantage of the invention that the process can be carried out over a wide temperature range extending from room temperature to 600° C., the range from 120 to 300° C. being particularly advantageous.

The hydrolysis can advantageously be carried out at atmospheric pressure, which is industrially advantageous, but it can also be carried out under subatmospheric or superatmospheric pressure, and the pressure range from 0.5 bar absolute to 50 bar absolute, especially from 1 to 5 bar absolute, is particularly advantageous.

A further particular advantage of the process according to the invention is its flexibility with respect to the components to be used, which may be both in the gas phase and the liquid phase.

In addition, the process of the invention is also useful for producing a very wide range of alcohols on a large scale in a simple and inexpensive manner from appropriately substituted hydrocarbyl halides.

The invention will now be illustrated by Examples and a schematic drawing of the process.

EXAMPLE 1

A plastics recycling plant 20 l/h process gas stream having a total chlorine content of 5000 mg/m3 (S.T.P.) made up in particular of methyl chloride, ethyl chloride, n-propyl chloride, n-butyl chloride and chlorobenzene is heated to 150° C. in a heat exchanger 1 and passed through a tubular reactor 2 70 cm in length and 1 cm in width at 150° and 0.1 bar absolute exit pressure. Tubular reactor 2 is packed with a hydrolysis activator consisting of activated carbon from 2 to 5 mm in particle size impregnated with 10% by weight of sodium hydroxide. The activated carbon IVP4 from Chemviron was used.

The halogen compounds used are converted with an almost quantitative yield, as is evident from Table 1 below:

TABLE 1

| Component | Entry mg of chlorine/ m3 (S.T.P.) | Exit mg of chlorine/ m3 (S.T.P.) | Conversion % |
| --- | --- | --- | --- |
| Methyl chloride | 3900 | 20 | 99.5 |
| Ethyl chloride | 500 | 5 | 99 |
| prim. Propyl chloride | 220 | 1 | 1 99.5 |

TABLE 1-continued

| Component | Entry mg of chlorine/ m3 (S.T.P.) | Exit mg of chlorine/ m3 (S.T.P.) | Conversion % |
|---|---|---|---|
| prim. Butyl chloride | 350 | 2 | 99.4 |
| Chlorobenzene | 5 | <1 | |

EXAMPLE 2

Example 1 is repeated with a reaction temperature of 250° C., affording the yields recited in Table 2:

TABLE 2

| Component | Entry mg of chlorine/ m3 (S.T.P.) | Exit mg of chlorine/ m3 (S.T.P.) | Conversion % |
|---|---|---|---|
| Methyl chloride | 4200 | 10 | 99.8 |
| Ethyl chloride | 550 | 2 | 99.6 |
| prim. Propyl chloride | 200 | <1 | >99.5 |
| prim. Butyl chloride | 320 | 1 | 99.7 |
| Chlorobenzene | 5 | <1 | |

EXAMPLE 3

Example 1 is repeated with the process gas stream replaced by a nitrogen stream and the chlorine compounds by the corresponding bromine compounds, affording the yields of Table 3.

TABLE 3

| Component | Entry mg of bromine/ m3 (S.T.P.) | Exit mg of bromine/ m3 (S.T.P.) | Conversion % |
|---|---|---|---|
| Methyl bromide | 5100 | 2 | 99.9 |
| Ethyl bromide | 600 | 1 | 99.8 |
| prim. Propyl bromide | 630 | <1 | >99.8 |
| prim. Butyl bromide | 770 | <1 | >99.8 |
| Bromobenzene | 50 | <1 | >98 |

The essence of the invention is that alkyl monohalides from, for example, processes gases are passed with water through a reactor packed with a hydrolysis activator comprising activated carbon impregnated with alkali metal hydroxide or alkaline earth metal hydroxide. The organic halides react almost quantitatively to form the corresponding alcohols, the halogen being obtained as an inorganic salt:

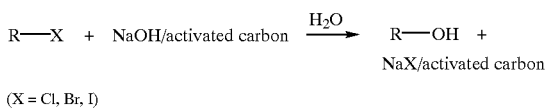

(X = Cl, Br, I)

Once the alkali metal hydroxide or alkaline earth metal hydroxide is consumed, the hydrolysis activator is purified by using water, for example, to flush out the accumulated inorganic halides, reactivated with alkali metal hydroxide or alkaline earth metal hydroxide solution and reused. The hydrolysis activator is thus simple to regenerate on an industrial scale.

Moreover, two or more reactors packed with hydrolysis activator can be connected in parallel to create a continuous process regime in which one reactor is operated in the dechlorination mode and a further in the regeneration mode.

We claim:

1. A process for hydrolyzing alkyl monohalides in a mixture comprising said alkyl monohalides in the presence of hydroxides and activated carbon, which comprises conducting the hydrolysis in the presence of water over activated carbon impregnated with alkali metal hydroxide and/ or alkaline earth metal hydroxide.

2. The process as claimed in claim 1, wherein the mixture comprises at least one $C_1$–$C_4$-alkyl monohalide, especially at least one $C_1$–$C_3$-alkyl monohalide.

3. The process as claimed in claim 1, wherein the activated carbon has been impregnated with from 1 to 40% by weight of alkali metal hydroxide and/or alkaline earth metal hydroxide, especially with from 5 to 25% by weight of alkali metal hydroxide or alkaline earth metal hydroxide.

4. The process as claimed in claim 3, wherein sodium hydroxide is used.

5. The process as claimed in claim 1, wherein the temperature is in the range from room temperature to 600° C., especially from 120 to 300° C.

6. The process as claimed in claim 1, wherein the pressure is in the range from 0.5 bar absolute to 50 bar absolute, especially from 1 to 5 bar absolute.

7. The process as claimed in claim 1, conducted in the gas phase.

8. The process as claimed in claim 1, conducted in the liquid phase.

9. Apparatus for carrying out the process of claim 1, comprising at least on tubular reactor packed with hydrolysis activator.

10. The method for preparing alcohols using the process of claim 1.

* * * * *

UNITED STATES PATENT AND TRADEMARK OFFICE
CERTIFICATE OF CORRECTION

PATENT NO.: 5,969,195

DATED: October 19, 1999

INVENTOR(S): STABEL et al.

It is certified that error appears in the above-identified patent and that said Letters Patent is hereby corrected as shown below:

Col. 4, claim 9, line 48, "on" should be --one--.

Signed and Sealed this

Eleventh Day of April, 2000

Attest:

Q. TODD DICKINSON

Attesting Officer

*Director of Patents and Trademarks*